US012582758B1

(12) United States Patent
Adams et al.

(10) Patent No.: US 12,582,758 B1
(45) Date of Patent: Mar. 24, 2026

(54) SURGICAL NOISE-LIMITING DEVICE

(71) Applicant: SILENT SURGICAL INC., St. Louis, MO (US)

(72) Inventors: Joshua David Adams, Webster Groves, MO (US); Yuping Derek Li, St. Louis, MO (US); Eric Leuthardt, St. Louis, MO (US)

(73) Assignee: SILIENT SURGICAL INC., St. Louis, MO (US)

( * ) Notice: Subject to any disclaimer, the term of this patent is extended or adjusted under 35 U.S.C. 154(b) by 0 days.

(21) Appl. No.: 19/299,793

(22) Filed: Aug. 14, 2025

Related U.S. Application Data

(63) Continuation of application No. 19/058,580, filed on Feb. 20, 2025.

(51) Int. Cl.
A61M 1/00 (2006.01)

(52) U.S. Cl.
CPC .......... A61M 1/7413 (2021.05); A61M 1/782 (2021.05); *A61M 2205/42* (2013.01)

(58) Field of Classification Search
CPC ............... A61M 1/7413; A61M 1/782; A61M 2205/42; A61M 1/74; A61M 1/741;

A61M 1/7411; A61M 1/742; A61M 1/76; A61M 1/71; A61M 1/7415; A61M 1/743; A61M 1/84; A61M 1/87; A61M 1/86; A61C 17/08; A61C 17/12; A61C 17/13; Y10S 604/902
See application file for complete search history.

(56) References Cited

U.S. PATENT DOCUMENTS

| | | | |
|---|---|---|---|
| 5,195,952 A | 3/1993 | Solnit et al. | |
| 5,899,884 A | 5/1999 | Cover et al. | |
| 7,306,577 B2 | 12/2007 | Lemoine et al. | |
| 2014/0135741 A1 | 5/2014 | Hamman et al. | |
| 2020/0009302 A1 | 1/2020 | Pyle | |
| 2023/0044805 A1* | 2/2023 | Donnelly | A61M 1/7411 |

* cited by examiner

*Primary Examiner* — Jason E Flick
(74) *Attorney, Agent, or Firm* — Oliff PLC

(57) ABSTRACT

A noise-reducing attachment for a surgical suction device having a valve operable by a finger. The attachment includes an airflow redirecting portion configured to overlay at least a portion of the valve; and at least one clip fixing portion configured to removably attach to a valve-housing portion of the surgical suction device. The airflow redirecting portion includes an opening extending from a top face to a bottom face thereof, and an axis extending through the opening is oriented at an acute of 10° to 80° relative to a longitudinal axis of the attachment.

20 Claims, 8 Drawing Sheets

SURGICAL NOISE-LIMITING DEVICE

This application is a continuation application of U.S. patent application Ser. No. 19/058,580, filed on Feb. 20, 2025, the entire disclosure of which is incorporated by reference in its entirety.

BACKGROUND

In many surgical procedures, for example brain and spine surgeries, a device with a suction capability is utilized in order to extract a fluid or other debris from the surgical site. Suction devices for clearing the surgical field are among the most commonly used tools because a clear view of the surgical field is essential.

Such devices, such as a Frazier suction instrument, are often connected to a suction source in the operating room in order to dynamically and efficiently remove blood, fluid, or other material such as bone fragments that are present in the surgical field. Such suction instruments operate by a user, for example, a surgeon, placing his/her finger on a valve in the device in order to manipulate the device and control suctioning force. However, when the valve is open while the device is in operation, an undesirably high level of noise may occur. Such noise may be present from the suction instrument, including suction tubing, a suction tip, and other components of the instrument.

Certain materials presently designed to reduce noise may limit airflow through the suction device. However, such materials may be bulky, may adversely affect the suction-ability of the device (thus, for example, not sufficiently reducing airflow when needed), and may even require the suction to be turned off in order to reduce noise.

SUMMARY

In some embodiments, a surgical suction device designed to address turbulent airflow at or near the valve portion is provided. Such a device may be provided in the form of an addition to an existing suction device, for example a clip-on device, or in the form of an integrated suction device that includes a turbulent-airflow reducing valve.

In some embodiments, a noise-reducing attachment to a surgical device is described. The noise-reducing attachment includes an airflow redirecting portion and a clip fixation portion. The airflow redirecting portion includes an opening extending from a top face of the airflow redirecting portion to a bottom face of the airflow redirecting portion. An axis extending through the opening from the top face to the bottom face is non-perpendicular to a longitudinal axis of the attachment.

In some embodiments, a surgical device is described. The surgical device includes a proximal portion having a suction tip, a valve-housing portion having a valve, a distal portion, and an attachment attached to the valve-housing portion. The attachment includes an airflow redirecting portion and a clip fixation portion. The airflow redirecting portion includes an opening extending from a top face of the airflow redirecting portion to a bottom face of the airflow redirecting portion. An axis extending through the opening from the top face to the bottom face is non-perpendicular to a longitudinal axis of the attachment.

In some embodiments, a surgical device is described. The surgical device includes a proximal portion having a suction tip, a valve-housing portion comprising a valve; and a distal portion. The valve-housing portion includes an airflow redirecting portion that includes the valve, the valve extending from a top face of the airflow redirecting portion to a bottom face of airflow redirecting portion. An axis extending through the valve from the top face to the bottom face is non-perpendicular to a longitudinal axis of the attachment.

BRIEF DESCRIPTION OF THE DRAWINGS

FIGS. 2A-2F show top perspective, bottom perspective, side, front and back and plan views, respectively, of the noise-reducing attachment according to some embodiments.

DETAILED DESCRIPTION

In the following description, numerous details are set forth to provide an understanding of the present disclosure. However, it may be understood by those skilled in the art that the methods of the present disclosure may be practiced without these details and that numerous variations or modifications from the described embodiments may be possible.

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the device and method described herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a range listed or described as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Furthermore, the subject matter of this application illustratively disclosed herein suitably may be practiced in the absence of any element(s) that are not specifically disclosed herein.

In some embodiments of the present application, an attachment capable of reducing noise generated by a suction device used in a medical procedure can be reduced. In some embodiments, noise reduction of 20 dBA (20 A-weighted decibels) or more can be achieved. Such a device may still allow for the suction device to function as intended, for example, the device may not interfere with the airflow through the suction parts of the suction device. Further, the attachment may allow for an ergonomic grip for comfort and operability by the user (e.g., a surgeon or other medical technician) can be achieved.

While the following examples referring to FIGS. 1-9 describes an attachment to a suction device, other embodiments, such as those described with respect to FIG. 10, describes a suction device with a modified valve housing portion, and thus, the attachment is omitted. In such an embodiment, some, all or more of the advantages described above may also be achieved.

Figure 1:
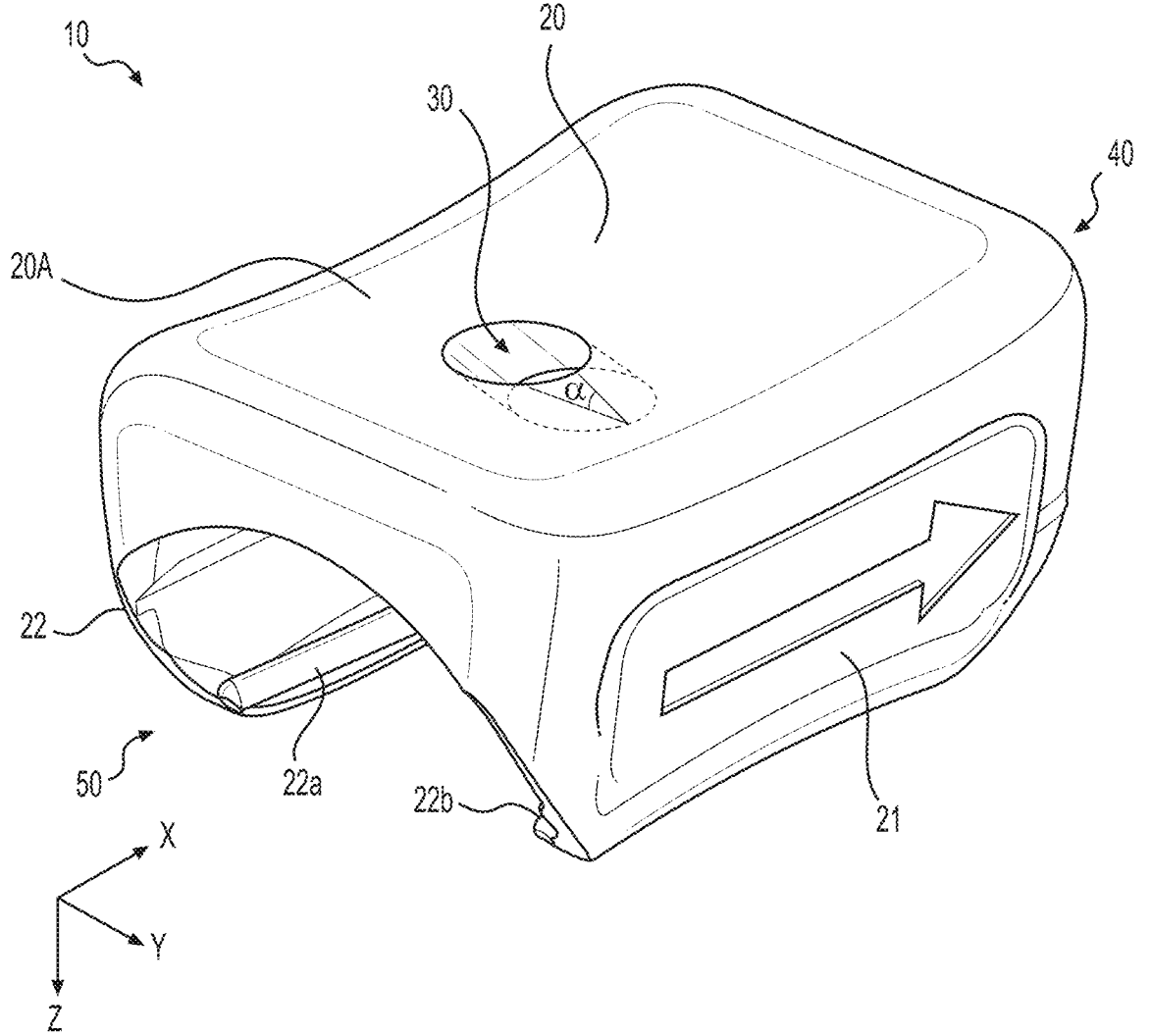
FIG. 1 shows a perspective view of a noise-reducing attachment according to some embodiments.

Referring to FIG. 1, an attachment 10 is shown. The attachment includes an airflow redirecting portion 20 and at least one clip fixing portion 21. In some embodiments, when oriented in a usable configuration, the airflow redirecting portion 20 may be an upper portion of the attachment 10, and the at least one clip fixing portion 21 may be on one or both sides of the attachment 10 and may extend substantially perpendicular, at least partially, to the airflow redirecting portion 20. However, the configuration of the at least one clip fixing portion 21 is not so limited and may be oriented in any configuration that can allow for fixing to a valve-housing portion of a surgical device. In some examples, the clip fixing portion 21 may be a side slide-on clip that slips on, for example, a tube or other part of a suction device, but in other embodiments, the clip fixing portion 21 may fix, or clip, the attachment 10 to a surgical device at the top, at the bottom, or at another practical attachment point. For example, a clamshell-type clip fixing portion 21, or a top down clip fixing portion 21 that fixes to one or both of a tube or a main body of a suction device may be used.

As shown by an example in FIGS. 2A and 2B, the airflow redirecting portion includes an opening 30 that extends from a top face 20a of the airflow redirecting portion 20 to a bottom face 20b. That is, the opening 30 may be fabricated to be entirely through the airflow redirecting portion 20.

In some embodiments, the attachment 10 generally, along with the airflow redirecting portion 20 and its opening, may be manufactured by 3D printing (additive manufacturing) via a stereolithography process (SLA/resin printing). In some embodiments, the attachment and/or some constituent components may be produced via injection molding and/or casting.

In some embodiments, the opening 30 has a substantially circular cross section in at least some locations along the z-axis (through) direction of the attachment. In other embodiments, the opening 30 may have a substantially elliptical cross section. In some embodiments, the offset nature of the opening, described later, may lead to differently-shaped cross sections along the z-axis direction. Other shaped-openings, such as a substantially square, substantially triangular, or other polygonal shaped openings as well as openings with some symmetric or asymmetric external cross-sectional concavity, may be utilized.

In some embodiments, the opening 30 is provided at a location closer to one of the front end 50 and back end 40 of the attachment. That is, the opening 30 may not be provided at the geometric center along the x-axis (lengthwise) direction of the attachment. For example, as shown in FIG. 1, the opening 30 is provided closer to the front end 50 than to the back end 40. In some embodiments, the opening 30 is provided in a location where its x-axis midpoint is approximately ⅔ of the distance between the front end 50 and the back end 40. Such a configuration may allow for a more appropriate fit on a valve provided within certain suction devices. In other embodiments, the opening 30 may be provided midway between the front end 50 and the back end 40 along the lengthwise direction of the attachment 10, or at a different location closer to the front end 50 than the back end 40, or even closer to the back end 40 than that shown in FIG. 1, with such configurations having an appropriate fit on certain suction devices. In some examples, the opening 30 is provided in a location that, when the attachment 10 is clipped to a suction device, is approximately centered over the valve in the suction device. The opening 30 then extends forwards, for example, toward a suction tip of a surgical device (described later), in order to allow an appropriate angle over the valve so as to reduce turbulent flow.

In some embodiments, the top face 20a of the attachment 10 has a concavity. That is, the top face 20a may not be entirely planar along either or both of the x-axis and y-axis (widthwise) direction of the attachment. In some embodiments, the top face 20a may be planar, have a convexity, or a mix of concavity, convexity and/or planar components to form a more complex geometry.

In the embodiment shown in FIG. 1, the top face 20a has a slightly concave shape along the x-axis. A lowest point of the top face 20a may be closer to the back end 40 along the x-axis direction than to the front end 50. In some embodiments, the lowest point is at or substantially near the position of the opening 30. Such a configuration may allow for a better fit with certain suction instruments, and may mirror the top face of certain suction instruments. For example, the curvature of the attachment 10 may be such to allow the bottom face 20b to mate well against a mating face of a valve portion of a suction device to which the attachment 10 clips. Such a configuration may also aid in noise reduction as compared to an entirely planar face.

In some embodiments, the opening 30 has a shape whereby it is asymmetrical along at least one of the x-axis, y-axis and z-axis. In some embodiments, and as shown in FIGS. 1, 2A and 2B and 2F, the opening 30 is such that when viewed in a plan view along a z-axis of the attachment, an axis extending through the opening is non-perpendicular to the x-axis (longitudinal axis) of the attachment 10. For example, an axis extending through the opening 30 from the top face 20a to the bottom face 20b is non-perpendicular to a longitudinal axis of the attachment 10.

In some embodiments, the opening 30 extends through the airflow redirecting portion 20 at a predetermined angle α with respect to the longitudinal axis of the attachment 10. As can be seen in FIG. 1, for example, the angle α may be an acute angle.

In some embodiments, the angle α may be from about 10 to about 80 degrees, or about 30 to about 60 degrees. In some embodiments, the angle α may be about 45 degrees.

The structure of the opening 30 may be such that the cross-section of the opening 30 at the top face 20a is offset, along the x-axis, from the cross-section of the opening 30 at the bottom face 20b.

The angle α of the opening 30 may be such that the angle leans toward a proximal end of the attachment 10. That is, the cross-section of the opening 30 at the top face 20a may be closer to the proximal end of the attachment than is the cross-section of the opening 30 at the bottom face 20b. In embodiments where the attachment 10 is attached to a suction device (e.g., a suction device 100 as described later), the angle may be such so the cross-section of the opening 30 at the top face 20a is closer to a suction tip than it is to tubing coupler. This may allow for an introduction of a more laminar flow as air enters the valve of the suction device, which advantageously reduces a turbulent flow, which particularly can otherwise be disadvantageously present at some points within the suction device, including a point slightly distal to the valve.

In some embodiments, the diameter of the cross-section of the opening 30 at the top face 20*a* may be equal to than the cross-section of the opening 30 at the bottom face 20*b*.

In some embodiments, the opening 30 has a generally circle shape when viewed top-down (e.g., along the z-axis of the attachment). That is, a cross-section of the opening 30 at the top face may be generally circular. Given the angle at which the opening 30 is fabricated, the cross-section at any point along the through-axis direction of the opening 30 may be elliptical. In describing the diameter of the opening 30 herein, the diameter at the top face 20*a* (e.g., at the point at which the opening 30 has a circle cross-section) is described. However, this may also be equivalent to a longest diameter of the elliptical cross-section when viewed along the through-axis direction. However, the shape of the opening 30 is not so limited, and other shapes when viewed down the z-axis may be present, such as ellipses, rectangles, combinations thereof with one or more fillets present, and the like. For example, other symmetric, asymmetric and amorphous shaped openings are within the scope of this disclosure.

In some embodiments, the diameter at the opening 30 at the top face 20*a* and/or the diameter of the opening at the bottom face 20*b* may be between 2 and 6 mm, or between 3 and 4 mm, or between 3.2567 mm and 3.5955 mm. In some embodiments, either or both diameters are sized to have a predetermined relationship with the diameter of a valve in a suction device to which the attachment 10 attaches.

In some embodiments, the diameter of the cross-section of the opening 30 at the top face 20*a* may be greater than or less than the cross-section of the opening 30 at the bottom face 20*b*. That is, the diameter at the top profile of the opening 30 may be different than the diameter at the bottom profile of the opening 30. In some embodiments, the diameter at the top profile of the opening 30 is larger or smaller than the diameter at the bottom profile of the opening 30, for example by up to 1% larger, or up to 5% larger, or up to 10% larger, or up to 25% larger, or up to 50% larger, up to 1% smaller, or up to 5% smaller, or up to 10% smaller, or up to 25% smaller, or up to 50% smaller. For example, the opening 30 may narrow constantly or at certain places as viewed downward (toward the bottom face 20*b*). In any event, the opening 30 may have a non-constant pitch and/or non-constant profile. In some embodiments where the configuration of the opening 30 is such that a diameter is not readily present, another dimension and/or shape of the opening 30 at the top face 20*a* may be the equal to or different from the dimension and/or shape of the opening 30 at the bottom 20*b*. An area is an example of a dimension that may be the same or different at the top face 20*a* as compared to the bottom face 20*b*.

Figure 2C:
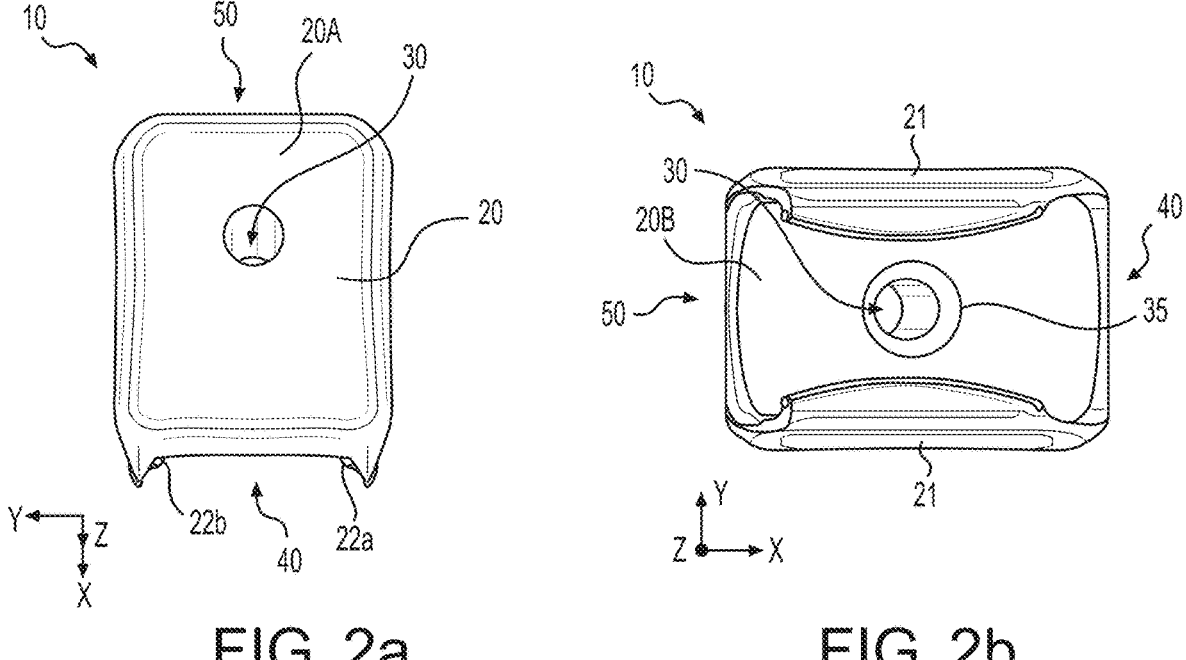
Figure 2C:
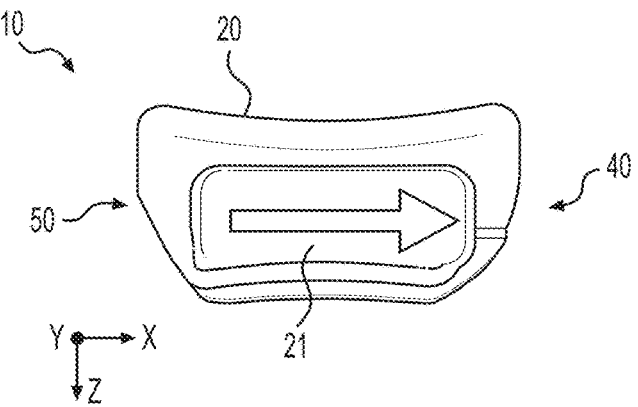
Figure 2D:
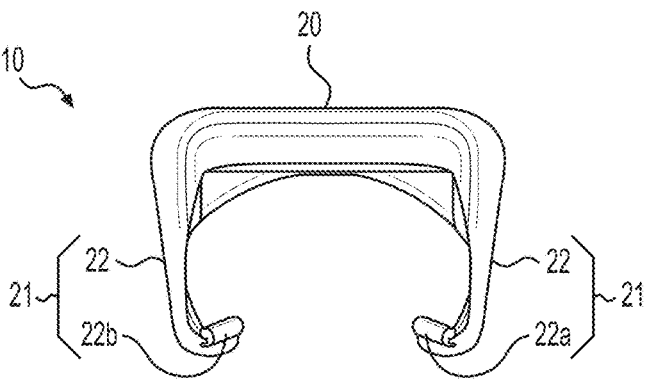
Figure 2D:
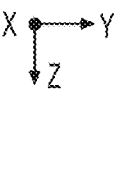
Figure 2E:
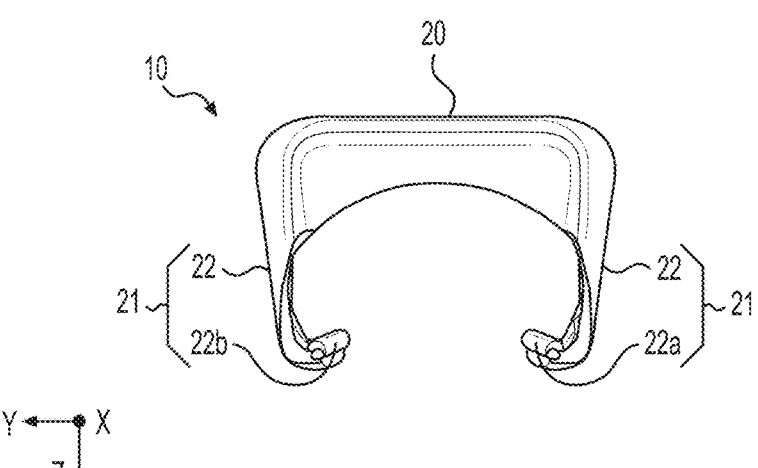
Figure 2F:
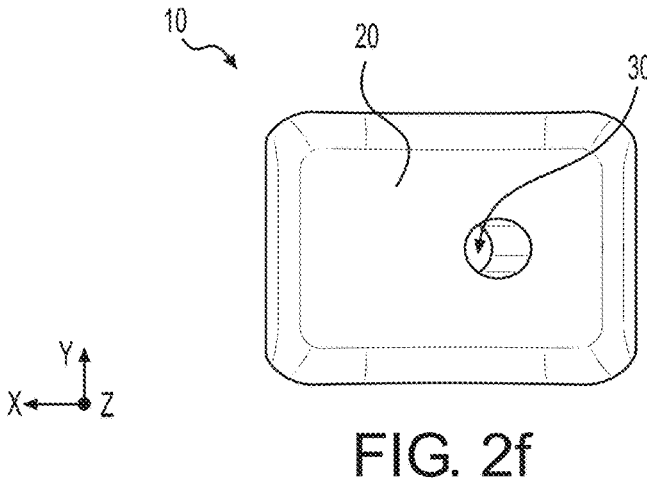

FIGS. 2C, 2D and 2E show side, front and back views of the attachment 10, respectively. As can be seen at least in FIGS. 2D and 2E, the clip fixing portions 21 of one embodiment may be side slip fixing portions that include side extension portions 22, each with a respective slip portion 22*a* and 22*b*. The slip portions 22*a* and 22*b* are configured to aid in attachment to a suction device, as described in more detail later. The slip portions 22*a* and 22*b* may be made of the same or substantially similar material as the rest of the attachment 10. In some embodiments, the side extension portions 22 extend inward from clip fixing portions 21. The extension inward may be at a right angle with respect to the clip fixing portions 21, or may be at an obtuse angle to allow for a smoother transition and a rounder fit to the suction device. Further, the slip portions 22*a* and 22*b* may extend upward in the z-axis direction from the side extension portions 22, and may have a substantially cylindrical cross section. The side extension portions 22 and slip portions 22*a* and 22*b* may be made of a relatively flexible material to allow for bendability to improve the attachability to the suction device. In some embodiments, the slip portions 22*a* and 22*b* have a greater thickness than that of the side extension portions 22.

In some embodiments, the material of the attachment 10 (including the slip portions 22*a* and 22*b*) may be a resin material. For example, the attachment 10 may be made entirely or partially of any one or more of an elastic 50A resin V2, a flexible 80A resin, a Tough1500 resin, and a Tough2000 resin. For clarity, a resin material also encompasses any type of polymer including injection molded polymers or other forms of manufacturing thermoplastics or thermoset plastics.

Figure 3:
FIG. 3 shows a side view of an attachment according to some embodiments.
Figure 3:
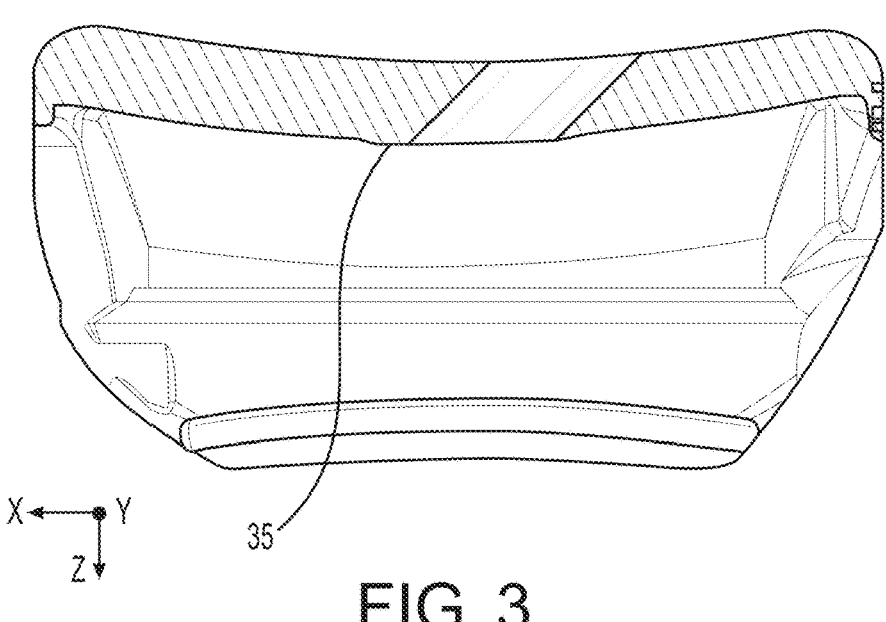
Figure 4:
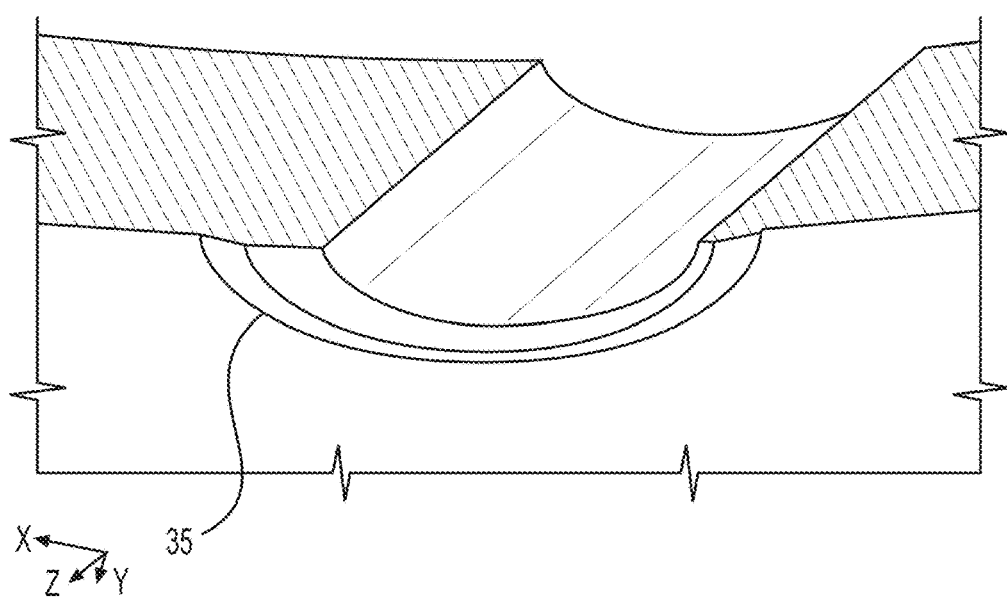
FIG. 4 shows an isometric view of an attachment according to some embodiments.

FIGS. 3 and 4 show a gasket 35 disposed around a circumference of the opening 30. The gasket may be any material within a predetermined distance from the opening, e.g., just below a bottom face 20*b* of the opening, or around some perimeter of the bottom face 20*b* of the opening. The gasket 35 may extend along an entire circumference of the opening 30. The gasket 35 may be made of the same material as that of the remainder of the attachment 10, but also may be made of a more flexible material (or less rigid) than a predetermined threshold, and/or that of the remainder of the attachment 10. In some embodiments, using a more flexible material for the gasket 35 may allow for more flexibility in the attachment 10 generally, while still allowing for improved sealing.

In some embodiments, the gasket is made of a base part material with one or both of 80A or 50A resin UV curable materials that are bonded directly to the base part. In embodiments, the gasket is provided around the opening 30 only at the bottom face 20*b* of the airflow redirecting portion 20, and not around the opening 30 at top face 20*a* of the airflow redirecting portion 20. In some embodiments, the gasket has a depth of from 0 to 0.5 mm, or from 0 to 0.2 mm, or about 0.1 mm. In some embodiments, using a gasket with a relatively softer material may allow for a gasket having a relatively larger thickness (>0.1 mm, or >0.2 mm, or up to 0.5 mm, or up to 1 mm) may have advantageous performance.

Figure 6:
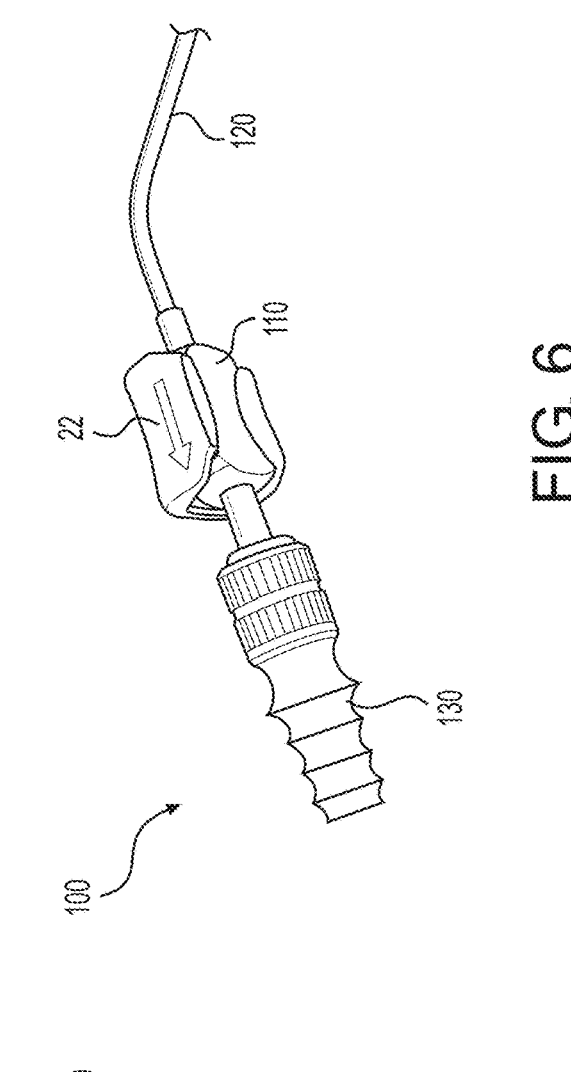
FIG. 6 shows an attachment attached to the surgical device according to some embodiments.
Figure 5:
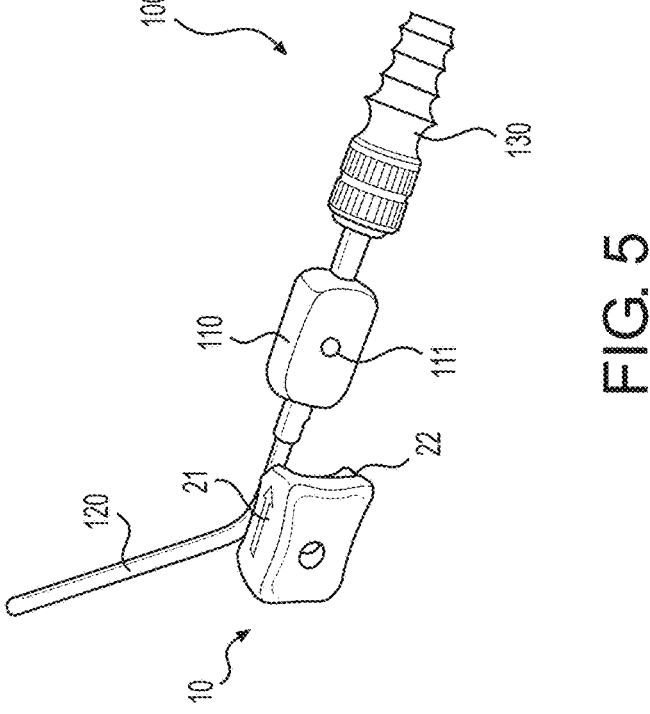
FIG. 5 shows an attachment alongside a surgical device according to some embodiments.

FIGS. 5 and 6 show an exemplary suction device 100 according to some embodiments. The suction device 100 may be a 14F Frazier suction device, a modified 14F Frazier suction device, a 12F Frazier suction device, a modified 12F Frazier suction device, a 10F Frazier suction device, a 10F blunt tip suction device, a 7F fenestrated tip suction device, or another suction device usable in a surgical procedure. Such suction devices 100 may be made of various materials, including a metal material.

In some embodiments, the suction device 100 includes, at its distal end, a tubing coupler 130 that ultimately connects to suction tubing that receives fluid such as blood from the target location or site. The suction tubing may be connected downstream to a suction removal station or waste site that can hold the extracted fluid for disposal. Proximal to the tubing coupler 130 is a middle portion 110 with a valve 111. Proximal to the middle portion 110 is a suction tip 120. The suction tip 120 may contact the target site to begin the target procedure. In some embodiments, the suction device 100 may have areas where turbulent airflow would exist, including at an area slightly distal to the valve 111.

The valve 111 may be operable, either manually by an operator placing his/her finger over the valve, or by another acceptable method. When the valve is closed (e.g., covered by the operator's finger), the suction at the target site may occur. However, there are many situations where the valve 111 may be in an open position while the suction device 100 is still on (e.g., in a standby mode ready to be used). In such cases, the suction device 100 may emit a large amount of noise, for example about 85 dBA. Such noise is undesirable and could lead to impairments for the operator, the patient, and others in the room.

Thus, as shown in FIGS. 5 and 6, the attachment 10 may be clipped onto the middle portion 110. The placement of the attachment 10 may be such that the opening 30 overlays at least some of, or all of, the valve 111. The attachment 10 may be clipped onto the middle portion 110 by means of the slip portions 22a and 22b, and/or by some or all of clip fixation portion 21.

Figure 7:
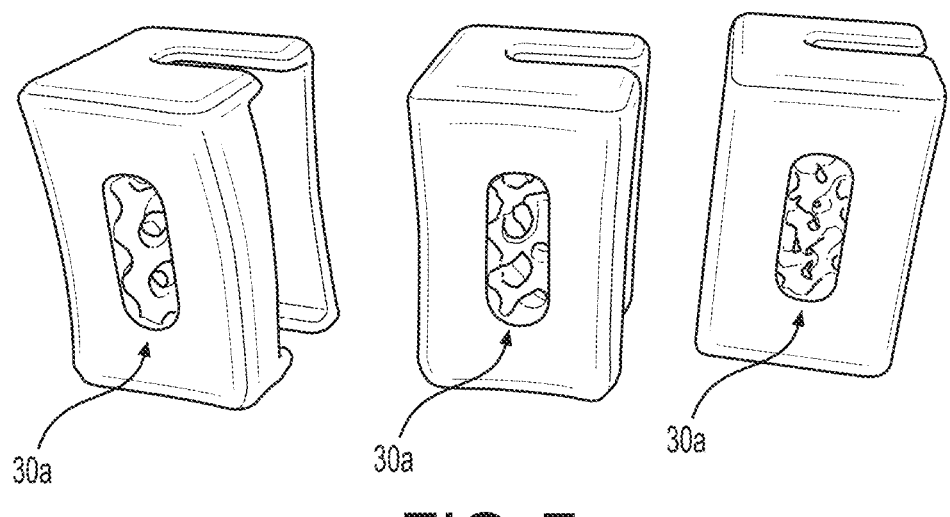
FIG. 7 shows a perspective view of a noise-reducing attachment according to some embodiments.
Figure 8:
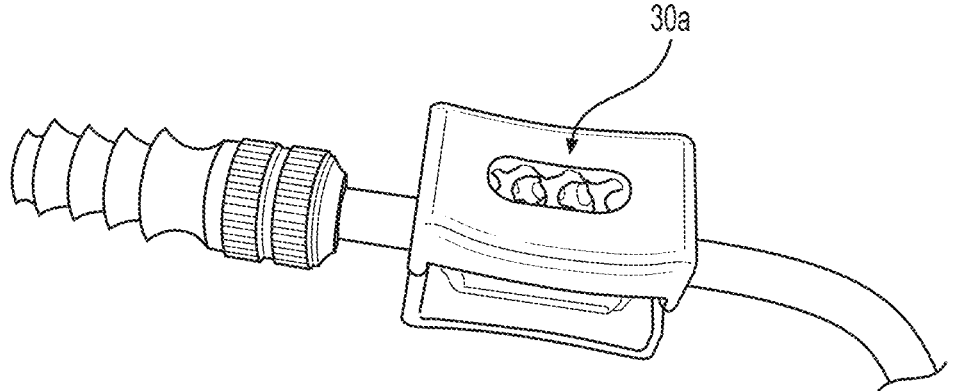
FIG. 8 shows an attachment attached to the surgical device according to some embodiments.

In some embodiments, as shown in FIGS. 7 and 8, the attachment 10 may be configured to have a gyroid structure 30A at its opening 30. The gyroid structure 30A may be a lattice structure with unit cells that tessellate in three dimensions. One gyroid of the gyroid structure 30A may be built from surfaces with the other structures, such as two structures are built as curvy, semi-cylindrical rods.

The configuration of the attachment 10 onto the suction device 100, including the orientation of the opening 30 configured as defined herein and the overlay or orientation of such an opening 30 with respect to the valve 111 may allow for advantageous noise reduction over a surgical device without the use of the attachment 10. As shown in the below Table 1, reduced noise from the exemplary embodiments exists. Such embodiments also allow for a reduction in bulkiness, an avoidance in reducing suctionability of the device, and no requirement to turn off the entire suction device to avoid noise, thus further improving over other devices.

TABLE 1

| Name | Body Material (gasket) | Attachment | Opening to atmosphere | (Vertical Thickness) Through-hole description |
|---|---|---|---|---|
| Baseline | Normal, open | 14 Fr Frazier suction hole/valve @ 520 mmHg suction | | |
| Baseline | Normal, open | 14 Fr Frazier suction hole/valve @ Significantly lower benchtop suction presure | | |
| Baseline | Empty Operating Room | | | |
| 1.3 | A | E | 4.5 mm × 11.5 mm Oval cut through straight to Suction Valve surface | (5.25 mm) Filled with ~55% dense Gyroid |
| 2.3 | A | E | 4.25 mm × 7.35 mm Oval cut through straight to Suction Valve surface. | (5.25 mm) Straight |
| 2.6 | A | E | 4.25 mm × 6.6 mm Oval with 0.75 mm flat cut off on top of oval and 2.5 mm radius fillet. | (5.25 mm) Straight after fillet |
| 2.B | A | E | 3.85 mm × 6 mm Oval with 0.75 mm flat cut off on top of oval | (5.25 mm) Straight |
| 2.G | A | E | 3.85 mm × 5.6 mm oval with 1.15 mm flat cut off on top of oval and additional 1.5 mm radius fillets applied to the top corners of the through hole. | (5.25 mm) Straight |
| 2.J | A | E | 4 mm × 10 mm Oval with varying fillets | (5.25 mm) 30° angle angled away from patient/suction tip (significantly reduced noise when installed backwards) |
| FrS.av | B | None | 3.3 mm × 5.3 mm Oval | (2.4 mm) predominantly 45° variable angle angled away from patient/suction tip. Suction tip side of hole terminated in sharp angle while tube connector side of hole utilited a variable radius fillet to gently introduce flow. |

| Name | Suction mating surface | Measurement dBA |
|---|---|---|
| Baseline | | |
| Baseline | | |
| Baseline | | |
| 1.3 | Flat mate to Frazier surface contour | 70.7 |
| 2.3 | Top of oval aligned to top of Frazier valve hole. Flat mate to Frazier surface contour | 66.3 |
| 2.6 | Flat mate to Frazier surface contour | 68.4 |
| 2.B | Flat mate to Frazier surface contour | 67.9 |
| 2.G | Flat mate to Frazier surface contour | 65.3 |
| 2.J | Flat mate to Frazier surface contour | 75.5 (65.6) |
| FrS.av | Not Applicable | ~56 dbA |

TABLE 1-continued

| | | | | |
|---|---|---|---|---|
| 7.C.1 | B | E | 3.75 mm circle profile | (5.25 mm) 45° angle toward patient/suction tip. Cross-section viewed from top: Circle. Cross-section viewed along axis of through-hole: ellipse. |
| 7.C.6 | B | F | 3.75 mm circle profile | (2 mm) 45° angle toward patient/suction tip. Cross-section viewed from top: Circle. Crossection viewed along axis of through-hole: ellipse. |
| 7.2.A | B | E | 3.75 mm circle profile | (2.25 mm) 45° angle toward patient/suction tip. Cross-section viewed from top: Circle. Cross-section viewed along axis of through-hole: elipse. |
| 7.4.A | B(B) | G | 3.75 mm circle profile | (2.25 mm) 45° angle toward patient/suction tip, Cross-section viewed from top: Circle. Cross-section viewed along axis of through-hole: elipse |
| 9.1 | B(B) | H | 3.5 mm circle profile | (2 mm) 45° angle toward patient/suction tip. Cross-section viewed from top: Circle. Cross-section viewed along axis of through-hole: elipse. |
| 9.9.C | B(B) | H | 3.5 mm circle profile | (1.75 mm) 45° angle toward patient/suction tip, Cross-section viewed from top: Circle. Cross-section viewed along axis of through-hole: ellipse |
| 106 | B(B) | H | 3.5 mm circle profile | (1.75 mm) 45° angle toward patient/suction tip. Through hole terminates to surface of suction with .25 mm filleted flap, directing air toward the final direction of flow, Cross-section viewed from top: Circle. Cross-section viewed along axis of through hole: ellipse. |

| | | |
|---|---|---|
| 7.C.1 | Flat mate to Frazier surface contour | 66 |
| 7.C.6 | Flat mate to Frazier surface contour | 62 |
| 7.2.A | Flat mate to Frazier surface contour | 63 |
| 7.4.A | Flat mate to Frazier surface contour with chamfered gasket with 0.75 mm width and 0.5 mm depth coming to a sharp edge at contact. | 62 |
| 9.1 | Flat mate to Frazier surface contour with chamfered gasket with 0.75 mm width and 0.5 mm depth coming to a sharp edge at contact. | 60 |
| 9.9.C | Flat mate to Frazier surface contour with chamfered gasket with 0.75 mm width and 0.5 mm depth coming to a sharp edge at contact. | 59 |
| 106 | Flat mate to Frazier surface contour with chamfered gasket with variable 0.5 mm to 1.3 mm width and 0.25 mm depth coming to a variable width contact surface between 0.08 mm and 0.9 mm. | 60 |

| | | | | |
|---|---|---|---|---|
| 112 | A(A) | H | 3.25 mm circle profile | (1.75 mm) 45° angle toward patient/suction tip. Through hole terminates to surface of suction with .25 mm filleted flap, directing air toward the final direction of flow. Cross-section viewed from top: Circle. Cross-section viewed along axis of through hole: ellipse. |
| 112.80A | A(C) | H | 3.25 mm circle profile | (1.75 mm) 45° angle toward patient/suction tip. Through hole terminates to surface of suction with .25 mm filleted flap, directing air toward the final direction of flow. Cross-section viewed from top: Circle. Cross-section viewed along axis of through hole: ellipse. |
| 123 | B(B) | H | 3.25 mm circle profile | (1.75 mm) 45° angle toward patient/suction tip. Cross-section viewed from top: Circle. Crossection viewed along axis of through-hole: ellipse. |
| 123.50A | B(D) | H | 3.25 mm circle profile | (1.75 mm) 45° angle toward patient/suction tip. Cross-section viewed from top: Circle. Crossection viewed along axis of through-hole: ellipse |
| 123F | B(B) | H | 3.25 mm circle profile | (1.75 mm) 45" angle toward patient/suction tip. Cross-section viewed from top: Circle. Crossection viewed along axis of through-hole: ellipse. |

TABLE 1-continued

| | | |
|---|---|---|
| 112 | Flat mate to Frazier surface contour with chamfered gasket with variable 0.25 mm to 1.05 mm width and 0.25 mm depth coming to a variable width contact surface between 0.08 mm and 0.9 mm. | 58 |
| 112.80A | Flat mate to Frazier surface contour with chamfered gasket with variable 0.25 mm to 1.05 mm width and 0.25 mm depth coming to a variable width contact surface between 0.08 mm and 0.9 mm. An additional coating of ~0.6 mm flexible 80A material was applied within ~4 mm of the opening. | 64 |
| 123 | Flat mate to Frazier surface contour with 10° chamfered gasket with variable 0.575 mm to 1.16 mm width and 0.25 mm depth coming to a variable width contact surface between 0.15 mm and 0.75 mm. (This gasket was shifted at 0.1 mm intervals in a series of unlisted tests to find the positioning that would dampen sound best for both 14 and 12 Fr sized frazier suctions) | 59 |
| 123.50A | Flat mate to Frazier surface contour with 10° chamfered gasket with variable 0.575 mm to 1.16 mm width and 0.25 mm depth coming to a variable width contact surface between 0.15 mm and 0.75 mm. (This gasket was shifted at 0.1 mm intervals in a series of unlisted tests to find the positioning that would dampen sound best for both 14 and 12 Fr sized frazier suctions). An additional coating of ~0.5 mm flexible 50A material was applied within ~4 mm of the opening. | 59 |
| 123F | Flat mate to Frazier surface contour with 10° chamfered gasket with variable 0.575 mm to 1.16 mm width and 0.25 mm depth coming to a variable width contact surface between 0.15 mm and 0.75 mm. (This gasket was shifted at 0.1 mm intervals in a series of unlisted tests to find the positioning that would dampen sound best for both 14 and 12 Fr sized frazier suctions) | 67.6 |

In the above Table 1, Under the Body Material (gasket) column, the letter identifies the material constituting the body. If in (parenthesis), the letter identifies the material constituting the gasket. Letter A corresponds to Tough1500 Resin. Letter B corresponds to Tough2000 Resin. Letter C corresponds to BioMed Flex 80A Resin. Letter D corresponds to Elastic 50A Resin.

In the above Table 1, the Attachment column refers to the type of attachment provided. Letter E corresponds to a side slide to tube attachment. Letter F corresponds to a clamshell-type attachment. Letter G corresponds to a top down to tube attachment. Letter H corresponds to a top down to main body attachment.

In examples named 1.3, 2.3, 2.6, 2.B, 2.G, 2.J and 123F, the testing performed was with a 14 French Frazier suction in full operating room vacuum pressure of 520 mmHg.

In examples named FrS.av, 7.C.1, 7.C.6, 7.2.A, 7.4.A and 9.1, the testing performed was with 14 French Frazier suctions in benchtop lab suction pressures. The suction pressure is unvalidated, but is below 520 mmHg.

In examples named 9.9.C, 106, 112, 123, and 123.50 A, the testing was with 14 and 12 (and some 10) French Frazier suctions (or an entirely fabricated new 14 French Frazier suction with a modified valve) in benchtop lab suction pressures. The suction pressure is unvalidated, but is below 520 mmHg.

Figure 9:
FIG. 9 are diagrams of exemplary attachments according to embodiments.

As can be seen in Table 1, the attachment 10 according to the Examples herein, some of which are also shown in FIG. 9, achieve a greater noise reduction than the baseline. In many embodiments, the reduction of noise led to a dbA reading significantly closer to the baseline of an empty operating room than to one with a suction device without a configuration of one of the embodiments. In some embodiments, such as in embodiments 123 and 123.50 A, the noise was reduced to 59 dBA. Thus, in some embodiments, a circle-angled opening 30 (e.g., one with a circle diameter when viewed from the top but an elliptical cross-section when viewed along the through-axis of the opening, as discussed previously) may have particularly advantageous properties. A diameter of about 3.25 may also lead to such advantageous properties. Further, a Flat mate to the surface of the suction device valve portion contour with 10° chamfered gasket with a 0.575 mm-1.16 mm width and 0.25 mm depth coming to a variable width contact surface between 0.15 mm-0.75 mm may have such advantageous properties. Generally speaking, the attachment 10 according to these examples and the embodiments described herein may also carry a unique advantage of being usable with already-in-use suction devices (such as Frazier suction devices) without any need for redesign or to create a new suction device. This can improve cost-effectiveness and incentivize users to utilize the device of the instant embodiments, so as to allow for noise-reduction properties without a significant operational change for the medical professional or hospital.

Figure 10A:
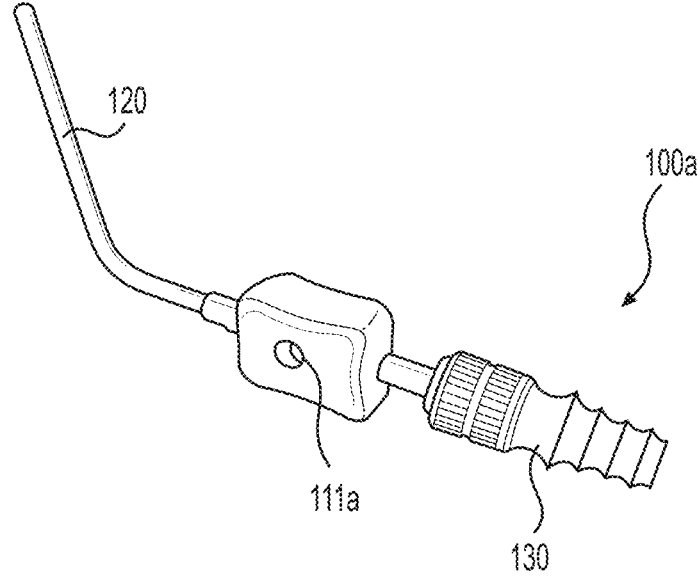
FIGS. 10A-10B show a surgical device with a valve housing portion according to some embodiments.
Figure 10B:
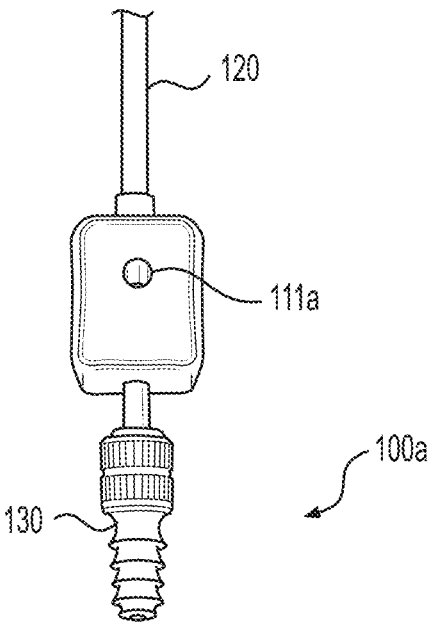

Further, in some embodiments, as shown in FIGS. 10A and 10B, instead of an attachment, the suction device 100a may be designed to include a valve opening portion 111a, with the valve opening portion 111a having a configuration similar to the opening 30 of FIGS. 1-2E. The valve opening portion 111a may otherwise have the same configuration as the opening 30 described in the embodiments above, and such properties are incorporated herein to this embodiment. That is, the attachment 10 from FIGS. 1-2E may not be included, and instead, an integrated suction device 100a may achieve noise reduction using an valve opening portion 111*a* in place of the valve 111 described with respect to FIGS. 5 and 6. An example in Table 1 corresponding to an embodiment with a valve opening portion 111*a* as part of an integrated suction device 100*a* is shown as example Fr.S.av.

Although the preceding description has been described herein with reference to particular means, materials and embodiments, it is not intended to be limited to the particulars disclosed herein; rather, it extends to all functionally equivalent structures, methods and uses, such are within the scope of the appended claims.

What is claimed is:

1. A noise-reducing attachment for a surgical suction device having a valve operable by a finger, the noise-reducing attachment comprising:

an airflow redirecting portion configured to overlay at least a portion of the valve; and at least one clip fixing portion configured to removably attach to a valve-housing portion of the surgical suction device, wherein the airflow redirecting portion includes an opening extending from a top face to a bottom face thereof, and the opening has a central axis extending from the top face to the bottom face, the central axis oriented at an angle of 10° to 80° relative to a longitudinal axis of the attachment.

2. The noise-reducing attachment according to claim 1, wherein the airflow redirection portion has a concave top face.

3. The noise-reducing attachment according to claim 1, further comprising a gasket on the bottom face of the airflow redirection portion, the gasket configured to engage with the valve of the surgical suction device.

4. The noise-reducing attachment according to claim 3, the gasket comprising a material having a rigidity lower than a predetermined threshold.

5. The noise-reducing attachment according to claim 1, wherein the opening has a non-constant pitch and/or a non-constant profile.

6. The noise-reducing attachment according to claim 5, wherein the opening has a non-constant pitch.

7. The noise-reducing attachment according to claim 1, wherein the axis extending through the opening is oriented at an angle of 30° to 60° relative to the longitudinal axis of the attachment.

8. The noise-reducing attachment according to claim 1, wherein the axis extending through the opening is oriented at an angle of about 45° relative to the longitudinal axis of the attachment.

9. The noise-reducing attachment according to claim 1, wherein the opening has a first diameter at the top face and a second diameter at the bottom face, the first diameter being equal to the second diameter.

10. The noise-reducing attachment according to claim 1, wherein the opening has a first dimension and/or shape at the top face and a second dimension and/or shape at the bottom face, the first dimension and/or shape being different from the second dimension and/or shape.

11. The noise-reducing attachment according to claim 1, wherein the opening has a diameter of between 3 mm and 4 mm.

12. The noise-reducing attachment according to claim 1, wherein the attachment comprises a resin material.

13. A noise-reducing attachment for a surgical suction instrument, comprising:

an airflow redirecting portion having a concave top face and configured to clip onto a valve-housing portion of the surgical suction instrument; and an angled opening extending through the airflow redirecting portion, wherein the angled opening has a central axis that extends at a predetermined acute angle from the concave top face of the airflow redirecting portion to a bottom face of the airflow redirecting portion, relative to a longitudinal axis of the noise-reducing attachment, and wherein the opening is positioned to overlay a valve of the surgical suction instrument to redirect airflow and reduce turbulent flow when the valve is open, the valve operable by a finger.

14. The noise-reducing attachment according to claim 13, further comprising a gasket on the bottom face of the airflow redirecting portion, the gasket configured to engage with the valve of the surgical suction instrument.

15. The noise-reducing attachment according to claim 13, wherein the airflow redirecting portion includes the angled opening extending from the concave top face to the bottom face, and an axis extending through the opening is oriented at an angle of 10° to 80° relative to the longitudinal axis of the noise-reducing attachment.

16. A surgical device, comprising:

a proximal portion having a suction tip;

a valve-housing portion comprising a valve operable by a finger;

a distal portion; and an attachment attached to the valve-housing portion, wherein the attachment comprises:

an airflow redirecting portion configured to overlay at least a portion of the valve; and at least one clip fixing portion configured to removably attach to the valve-housing portion of the surgical device, wherein the airflow redirecting portion includes an opening extending from a top face to a bottom face thereof, and the opening has a central axis extending from the top face to the bottom face, the central axis oriented at an angle of 10° to 80° relative to a longitudinal axis of the attachment.

17. The surgical device according to claim 16, wherein the suction tip is configured to suction a material from a target location of a patient.

18. The surgical device according to claim 16, wherein the distal portion includes a suction tubing.

19. The surgical device according to claim 18, wherein the suction tubing is configured to be connected to a suction removal station that holds suctioned material.

20. A surgical device, comprising:

a proximal portion having a suction tip;

a valve-housing portion comprising a valve; and a distal portion, wherein the valve-housing portion includes an airflow redirecting portion that includes the valve, the valve extending from a top face of the airflow redirecting portion to a bottom face of airflow redirecting portion, and a central axis extending from a top face of the airflow redirecting portion to a bottom face of the redirecting portion oriented at an angle of 10° to 80° relative to a longitudinal axis of the surgical device.

\* \* \* \* \*